United States Patent
Sahi et al.

(10) Patent No.: US 12,297,476 B2
(45) Date of Patent: May 13, 2025

(54) METALLIC NANOPARTICLES AND METHODS OF MAKING AND USING THE SAME

(71) Applicants: Saint Joseph's University, Philadelphia, PA (US); Western Kentucky University Research Foundation, Bowling Green, KY (US)

(72) Inventors: Shivendra V. Sahi, Moorestown, NJ (US); Nilesh Sharma, Bowling Green, KY (US); Sinilal Bhaskaran, Kerala (IN)

(73) Assignees: Saint Joseph's University, Philadelphia, PA (US); Western Kentucky University, Bowling Green, KY (US)

( * ) Notice: Subject to any disclaimer, the term of this patent is extended or adjusted under 35 U.S.C. 154(b) by 706 days.

(21) Appl. No.: 17/403,978

(22) Filed: Aug. 17, 2021

(65) Prior Publication Data

US 2022/0049277 A1    Feb. 17, 2022

Related U.S. Application Data

(60) Provisional application No. 63/066,682, filed on Aug. 17, 2020.

(51) Int. Cl.
*C12P 3/00* (2006.01)
*A61K 33/242* (2019.01)
*B82Y 5/00* (2011.01)
*B82Y 40/00* (2011.01)
*C01G 7/00* (2006.01)

(52) U.S. Cl.
CPC .............. *C12P 3/00* (2013.01); *A61K 33/242* (2019.01); *C01G 7/00* (2013.01); *B82Y 5/00* (2013.01); *B82Y 40/00* (2013.01); *C01P 2004/04* (2013.01); *C01P 2004/30* (2013.01); *C01P 2004/62* (2013.01); *C01P 2004/64* (2013.01)

(58) Field of Classification Search
None
See application file for complete search history.

(56) References Cited

U.S. PATENT DOCUMENTS 8,257,670 B1 *  9/2012  Dakshinamurthy .... B22F 1/052
                                                      75/343
8,569,063 B1 * 10/2013  Sahi ........................ B82Y 40/00
                                                      977/727

OTHER PUBLICATIONS

Armendariz et al. Journal of Nanoparticle Research (2004), 6(4), 377-382 (Year: 2004).*

* cited by examiner

*Primary Examiner* — Christian L Fronda
(74) *Attorney, Agent, or Firm* — Fox Rothschild LLP

(57) ABSTRACT

The invention relates to metallic nanoparticles made by that have been made in a plant cell suspension, and methods of making the metallic particles.

18 Claims, 4 Drawing Sheets

METALLIC NANOPARTICLES AND METHODS OF MAKING AND USING THE SAME

CROSS-REFERENCE TO RELATED APPLICATIONS

This application claims benefit of priority to U.S. Provisional Application No. 63/066,682, filed Aug. 17, 2020. The contents of which are hereby incorporated by reference.

FIELD

The present disclosure relates to metallic particles and methods of manufacturing the same using a plant cell suspension medium. The present invention also provides for novel uses of such metallic particles.

BACKGROUND

Nanotechnology is a relatively new and fast-growing field, enabling the generation of nanomaterials with unique optoelectronic and physicochemical attributes. These nanomaterials are useful for a variety of applications in medicine, consumer goods, heavy industry, information and communication technologies, optoelectronic devices, environment-friendly energy systems, chemical catalysis, and other fields. Since the early 1990s, a great deal of research has been conducted into various types of nanomaterials, which has led to a better understanding of the materials. One type of material that has been of interest in this technology is gold. Due to their unique physicochemical properties, gold nanoparticles (AuNPs) have been found to be useful for a variety of pharmaceutical and biomedical applications, such as for example, chemical sensing, biological imaging, drug delivery, and cancer treatment. Because they are relatively easy to conjugate with different molecular and chemical entities, and amenable to alterations in their optical properties, gold nanoparticles are also particularly useful for photomedicine, such as cancer imaging, photothermal ablation, and photodynamic therapy.

Conventional techniques for synthesis of gold nanoparticles employ physical or chemical methods. However, there are disadvantages associated with both of these type of methods. For example, physical methods, including evaporation and laser ablation, are expensive and laborious. Meanwhile, chemical methods involve the use of strong reducing agents and are potentially hazardous to the environment. Whole plants have been manipulated for the fabrication of nanomaterials, in an effort to provide an eco-friendly alternative to the chemical and physical methods. However, these efforts suffered from the inability to isolate the nanoparticles, low yield, as well as the inability to control the nanoparticle shape and size, which imposes limitations on their utility. Therefore, there remains a need for alternative methods to produce gold nanoparticles.

SUMMARY OF THE INVENTION

This patent document discloses novel metallic nanoparticles and novel methods of manufacturing the same by using a medium containing a suspension of plant cells, and methods of using such metallic particles.

A first aspect of the disclosure provides a method of synthesizing metallic nanoparticles by: providing at least a portion of at least one plant, placing the at least one portion of the plant in a suitable cell suspension medium, to form a plant cell suspension, forming a plant cell suspension, adding at least one metal salt solution comprising a metal salt to the plant cell suspension, forming metallic nanoparticles, and isolating the metallic nanoparticles from the plant cell suspension by at least one of sonication or centrifugation, and at least one of a gel filtration column or molecular sieve chromatography.

In some embodiments, the cell suspension medium contains at least one of, a macronutrient, micronutrient, vitamin, amino acid, nitrogen supplement, carbon source, energy source, organic supplement, growth regulator, or solidifying agent. In some embodiments, the cell suspension medium contains, or has added to it, at least one of, a macronutrient, micronutrient, vitamin, amino acid, nitrogen supplement, carbon source, energy source, organic supplement, growth regulator, or solidifying agent or any combinations thereof. In some embodiments, the method further includes the step of adding at least one growth regulator to the cell suspension medium.

In some embodiments, the growth regulator is an auxin, cytokinin, gibberellin, abscisic acid, or a combination thereof. In some embodiments, the growth regulator is indole-3-acetic acid (IAA), 6-benzyloaminopurine (BAP or BA), or a combination thereof. In some embodiments, the method further includes the step of adding at least one growth regulator, carbohydrate and solidifying agent to the cell suspension medium. In some embodiments, the method further includes the step of drying the metallic nanoparticles.

In some embodiments, the portion of the plant is at least a portion of a leaf, stem, root, flower, fruit, seed, or a combination thereof. In some embodiments, the plant cells are cells of a plant belonging to a plant family of Fabaceae, Solanaceae, Lamiaceae, Asteraceae, or a combination thereof. In some embodiments, the plant cells are cells of a plant of a type *Medicago sativa, Sesbania drumondii, Nicotiana tabacum, Ocimum sanctum, Mentha* species, *Artemisia annua*, or a combination thereof. In some embodiments, the metal salt is a salt of a heavy metal. In some embodiments, the metal salt is a salt of gold, copper, titanium, aluminum, or a combination thereof. In some embodiments, the metal salt a chloride, acetate, carbonate, citrate, cyanide, fluoride, nitrate, oxide, phosphate, sulfate, or a combination thereof. In some embodiments, metal salt is potassium gold chloride (KAuCl4). In some embodiments, the metallic nanoparticles have a morphology that is spheres, triangles, pentagons, pentagonal pyramids, hexagons, rods, rhomboids, nanoplates, or a combination thereof. In some embodiments, the metallic nanoparticles have a length ranging from about 2 nm to about 250 nm. In some embodiments, the metallic nanoparticles have a length ranging from about 5 nm to about 75 nm. In some embodiments, the metallic nanoparticles have a length ranging from about 15 nm to about 50 nm. In some embodiments, at least one of the morphology or size of the metallic nanoparticle can be controlled by adjusting the concentration of the metal salt solution in the plant cell suspension. In some embodiments, the concentration of the metal salt solution in the plant cell suspension ranges from less than 5 ppm to about 350 ppm. In some embodiments, the concentration of the metal salt solution in the plant cell suspension ranges from less than 10 ppm to about 250 ppm. In some embodiments, the concentration of the metal salt solution in the plant cell suspension ranges from less than 25 ppm to about 150 ppm. In some embodiments, the concentration of the metal salt solution in the plant cell suspension ranges from about 125 ppm to about 150 ppm.

In some embodiments, the metallic nanoparticles are isolated from the plant cell suspension using a process that is at least one of at least one of sonication or centrifugation, and at least one of a gel filtration column or molecular sieve chromatography. In some embodiments, each metallic nanoparticle has attached thereto at least one moiety. In some embodiments, the moiety is an aliphatic alcohol, alkyl, hydroxyl, amino, functional group, or a combination thereof.

A second aspect of the disclosure provides a cell suspension made by the method of the first aspect.

A third aspect of the disclosure provides a cell suspension containing plant cells, a cell suspension medium, and a metal salt solution. In some embodiments, the cell suspension further contains at least one of a growth regulator, carbohydrate, or solidifying agent. In some embodiments, the cell suspension further contains metallic nanoparticles. In some embodiments, the metallic nanoparticles are located within the plant cells.

A fourth aspect of the disclosure provides a composition containing metallic nanoparticles made according to the method of the first aspect. In some embodiments, the portion of the plant is from a plant belonging to a plant family of Fabaceae, Fabaceae, Solanaceae, Lamiaceae, Asteraceae, or a combination thereof. In some embodiments, the portion of the plant is from a plant selected from *Medicago sativa*, *Sesbania drumondii*, *Nicotiana tabacum*, *Ocimum sanctum*, *Mentha* species, *Artemisia annua*, or a combination thereof. In some embodiments, the metal salt is a salt of a heavy metal. In some embodiments, metal salt is a salt of gold, copper, titanium, aluminum, or a combination thereof. In some embodiments, the salt in the metal salt is a chloride, acetate, carbonate, citrate, cyanide, fluoride, nitrate, oxide, phosphate, sulfate, or a combination thereof. In some embodiments, the metallic nanoparticles have a morphology that is spheres, triangles, pentagons, pentagonal pyramids, hexagons, rods, rhomboids, nanoplates, or a combination thereof. In some embodiments, the metallic nanoparticles have a length ranging from about 2 nm to about 250 nm. In some embodiments, the metallic nanoparticles have a length ranging from about 5 nm to about 75 nm. In some embodiments, the metallic nanoparticles have a length ranging from about 15 nm to about 50 nm.

A fifth aspect of the disclosure provides a method of using the metallic nanoparticles in treating a subject in need thereof by administering to the subject a pharmaceutically sufficient amount of the metallic nanoparticles.

BRIEF DESCRIPTION OF THE DRAWINGS

FIGS. 1A, 1B, 1C and 1D represent TEM images of nanoparticles synthesized using 10, 50, 100 and 200 ppm of $KAuCl_4$, respectively; FIG. 1E represents a chart of the size of particles plotted against different concentrations of $KAuCl_4$ used for induction (values are means of 1,000 particles ±SE; since p value is lower than 0.05 and the value of F is above F Crit in ANOVA, the difference between the groups is significant); FIG. 1F represents a chart of the abundance of gold nanoparticles (AuNPs) of different geometrical shapes plotted against changing pH of the medium; and FIGS. 1G and 1H represent TEM (Transmission Electron microscope) images of nanoparticles synthesized in the culture medium at pH 5.8 and 3.9, respectively (in ANOVA, p value is lower than 0.05 and F value is less than F Crit validating insignificant difference between the groups; values are means of 1,000 particles ±SE).

FIG. 2A represents a chart showing UV-Vis absorbance spectrum of the particles eluted from the gel permeation column showing peak around 540 nm; FIG. 2B represents a chart showing distribution of absorbance peaks of the fractions eluted from gel permeation column indicating size similarity among the particles; FIG. 2C represents a chart showing FT-IR transmittance peaks of cell cultured AuNPs (compared with chemically synthesized AuNPs (csAuNPs)) demonstrating the presence of aliphatic alcohol (1480-1405, 1075-100 cm−1), alkyl (2990-2855, 1485-1415 cm−1), hydroxyl/amino groups (3540-3200, 1205-885 cm−1) on particle surface; FIG. 2D represents a TGA (Thermogravimetric analysis) plot showing the disintegration of particle surface functional groups; FIG. 2E represents a chart showing absorbance at 660 nm of the reaction with cell cultured AuNPs (ccAuNPs) as catalyst, plotted against the respective control, demonstrating that reaction over a period of 1 hr shows the enhancement rate of 33%.

FIGS. 3A, 3D and 3G represent stereo TEM images of triangle (3A), pentagon (3D) and hexagon (3G) shaped AuNPs captured at +5°; FIGS. 3B, 3E and 3H represent stereo TEM images of the triangle, pentagon and hexagon shaped AuNPs captured at −5°, FIGS. 3C, 3F and 3I represent computer images of the triangle, pentagon and hexagon shaped AuNPs identifying them as tetrahedron, pentagon and pentagonal prism shapes, respectively; and FIGS. 3J, 3K, 3L, 3M, 3N and 3O represent TEM images of two-sided pentagonal pyramids at +45° (FIGS. 3J and 3M), 0° (FIGS. 3K and 3N) and −45° (FIGS. 3L and 3O) illustrating how the particles can be identified as rhomboids in regular TEM. Arrows indicate the particles under observation.

FIG. 4A represents a chart showing cell death induced due to the toxicity of ccAuNPs on HEp-2 cells; FIG. 4B represents a chart showing cell death induced due to the toxicity of csAuNPs, plotted as percentage of cell viability against the concentrations of nanoparticles used; FIG. 4C represents a chart showing cell death in 4T-1 cells exposed to ccAuNPs; FIG. 4D represents a chart showing cell death in 4T-1 cells exposed to csAuNPs. FIG. 4E represents a chart showing serum levels of cytokines: IL-2, IL-4, IGF-1, GMCSF, Rantes, MCP-1, EGF and VEGF in mice following exposure of csAuNPs (center bar bar), ccAuNPs (right bar) and control (no nanoparticles, left bar). The variations between groups are statistically not significant (t-test; p>0.05).

DETAILED DESCRIPTION OF THE INVENTION

Figures 1A, 1B, 1C, 1D, 1E, 1F, 1G, 1H:
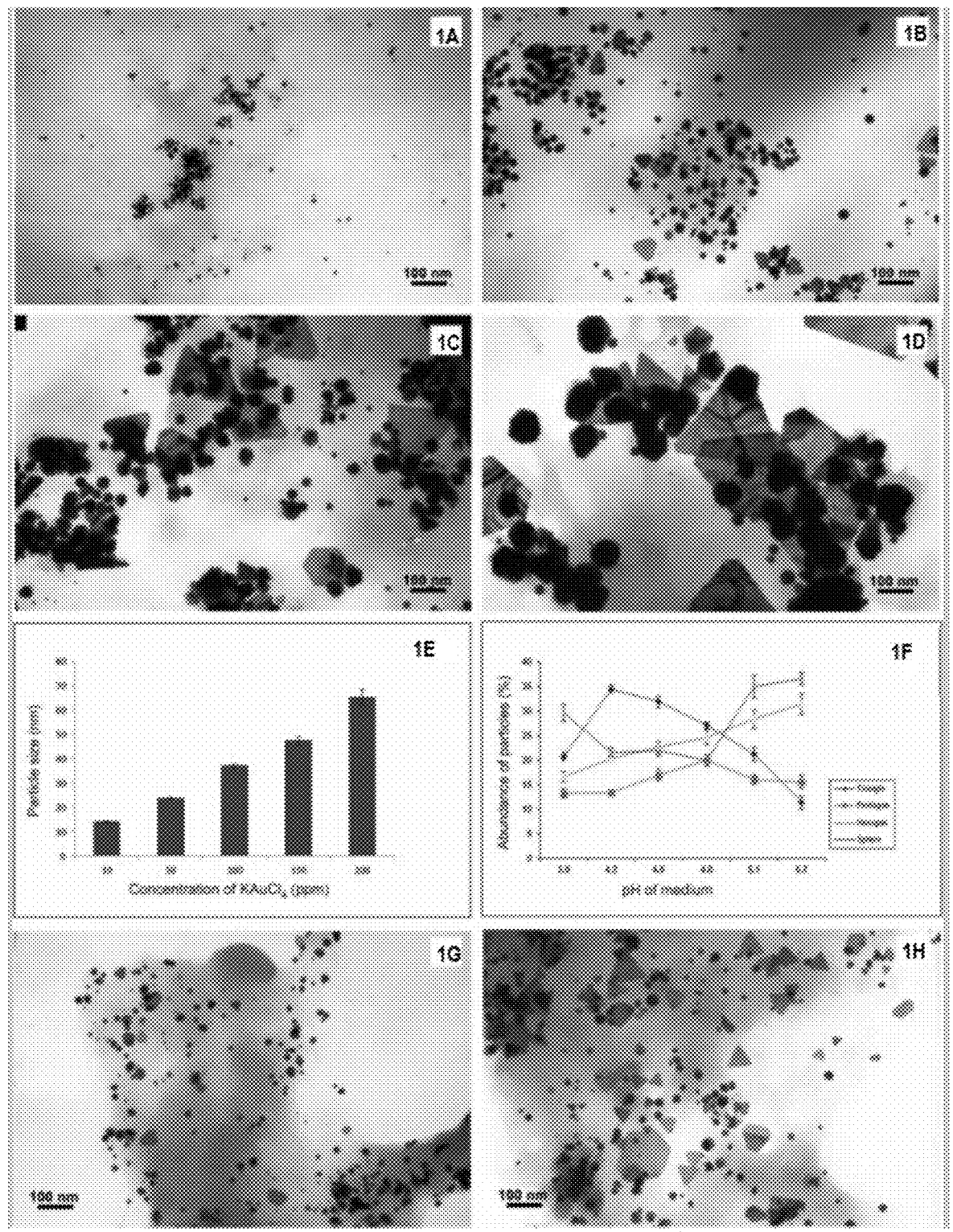
FIGS. 1A-1H represent images showing the variation in the size and geometry of metallic nanoparticles synthesized under different reaction conditions.

The present disclosure relates to metallic nanoparticles, and methods of making the metallic nanoparticles. In an effort to overcome the prior art disadvantages, an eco-friendly alternative is described herein, which involves causing whole living plant cells to uptake the gold. The present inventors unexpectedly discovered that in at least one embodiment, at least one of the disadvantages of the prior art methods can be overcome by employing suspended plant cells in a growth medium containing a metal salt solution, to make metallic nanoparticles.

The metallic nanoparticles of the present disclosure are made by adding at least a portion of a plant to a cell suspension medium, thereby creating a plant cell suspension, and adding a metal salt solution to the plant cell suspension. Cell suspension culture allows the growth of a plurality of intact cells under controlled conditions, similar to bacterial broth culture. The metal salt solution enters the plant cells, where the gold nanoparticles are made within the plant cells. Without intending to be held to any particular theory, it is believed that the metallic nanoparticles are made by inducing the plant cells to make the metallic particles.

The at least one portion of a plant can be one or more portions of a living plant, and can come from any part of the plant. In some embodiments, the at least one portion of the plant is an explant. By "explant" is meant herein, tissue obtained from a plant that is to be cultured. In some embodiments, the explant is a portion of a plant part, such as for example, a portion of a leaf, stem, root, flower, fruit, seed, or combination thereof. In some embodiments, the explant is a whole plant part, such as for example, a whole leaf, stem, root, or combination thereof. In some embodiments, the at least one portion of a plant is a whole plant, such as for example a plant seedling. In some embodiments, the size of the portion of the plant is from about 0.5 cm to about 2 cm.

Any suitable plant can be used to make the metallic nanoparticles. Suitable plants have cells that are capable of intaking a metal salt and making metallic nanoparticles within the cells. Since the plant cells are used to intake metal salts, the plant cells' toxicity response to the metal in the metallic salt should be sufficiently low for the plant cells to intake the metal salt without sustaining substantial cell damage. In some embodiments, the plant is a leguminous plant, for example, *Medicago sativa, Sesbania drumondii, Trifolium repens, Trifolium pretense*, or a combination thereof. In some embodiments, the plant is a *Medicago sativa* (alfalfa) plant. *Medicago sativa* possesses a reduced toxicity response toward heavy metals, including gold, as compared to many other plant types, providing it with the unusual potential for hyperaccumulation of metals. By "leguminous plant" is meant a plant belonging to the family Fabaceaea. Members of the Fabaceaea include, for example, *Glycine max* (soybean), *Phaseolus* (beans), *Pisum sativum* (pea), *Cicer arietinum* (chickpeas), *Medicago sativa* (alfalfa), *Arachis hypogaea* (peanut), *Ceratonia siliqua* (carob), *Glycyrrhiza glabra* (liquorice), *Cytisus scoparius* (broom), *Robinia pseudoacacia* (black locust), *Ulex europaeus* (gorse) and *Pueraria montana* (kudzu). In some embodiments, the leguminous plant belongs to the genus *Astragalus Acacia, Indigofera, Crotalaria, Mimosa, Trifolium repens, Trifolium pretense, Vicia faba, Arachis hypogea, Lens culinaris* or *Vigna radiata, Vigna unguiculata*. In some embodiments, the plant is a species from a non-leguminous plant family such as for example, *Nicotiana tabacum, Ocimum sanctum, Mentha piperita*, and *Artemisia annua*, or a combination thereof. In some embodiments, a combination of different plant types are used to make the metallic nanoparticles.

The plant cell medium used to create the plant cell culture may be any medium capable of culturing plants. Such media typically contain at least one of, macronutrients (such as for example, besides carbon (C), hydrogen (H) oxygen (O), nitrogen (N), phosphorus (P), potassium (K), calcium (Ca), magnesium (Mg), sulphur (S), or combinations thereof); micronutrients (such as, for example, iron (Fe), manganese (Mn), zinc (Zn), boron (B), copper (Cu) and molybdenum (Mo), or combinations thereof); vitamins (such as, for example, hiamin (B1), nicotinic acid, pyridoxine (B6), biotin, folic acid, ascorbic acid, pantothenic acid, tocopherol (vitamin E), riboflavin, p-amino-benzoic acid, or combinations thereof); amino acids (such as, for example, casein hydrolysate amino acids, L-glutamine, L-asparagine, glycine, adenine, L-arginine, cysteine, L-tyrosine or combinations thereof); nitrogen supplements, source(s) of carbon, organic supplements (such as, for example, natural substances or extracts such as protein hydrolysates, coconut milk, yeast extract, malt extract, ground banana, orange juice, tomato juice, activated charcoal or combinations thereof); growth regulators (such as, for example, auxins (such as, for example, indole-3-acetic acid (IAA), indole-3-butricacide (IBA), 2,4-dichlorophenoxy-acetic acid (2,4-D), naphthalene-acetic acid (NAA), 4-chlorophenoxy acetic acid or p-chloro-phenoxy acetic acid (4-CPA, pCPA), 2,4, 5-trichloro-phenoxy acetic acid (2,4,5 T), 3,6-dichloro-2-methoxy-benzoic acid (dicamba) and 4-amino-3,5,6-trichloro-picolinic acid (picloram) or combinations thereof); cytokinins (such as for example, BAP or BA (6-benzyloaminopurine), 2iP (6-dimethylaminopurine), kinetin (N-2-furanylmethyl-1H-purine-6-amine), Zeatin (6-4-hydroxy-3-methyl-trans-2-butenylaminopurine), TDZ (thiazuron-N-phenyl-N-1,2,3 thiadiazol-5ylurea), or combinations thereof); gibberellins (such as for example, any one of $GA_1$ through $GA_n$), abscisic acid, or combinations thereof); a carbon or energy source (such as, for example, carbohydrates such as for example, sucrose, glucose, fructose, lactose, galactose, maltose, starch, or combinations thereof); or solidifying agents (such as, for example, gelling agents such as agar, agarose, gellan gum, or combinations thereof). Commercial plant culture media are well known to those of ordinary skill in the art, such as for example, MS (Murashige and Skoog) medium, Gamborg's medium, Chu (N6) medium, Nitsch medium, or Schenk & Hidebrandt medium.

The plant cell culture can contain, or be supplemented with any of the abovementioned components, or with other components, many of which are well known in the art. In some embodiments, the plant cell medium either contains, or is supplemented with at least one plant growth regulator. The growth regulator can be used alone, or in combination with other growth regulators. In some embodiments, the growth regulator is at least one auxin, and at least one cytokinin, or a combination thereof. In some embodiments, the growth regulator is at least one of IAA or BA.

In some embodiments, the plant cells are suspended in an MS medium supplemented with at least one of a growth regulator, a carbohydrate, and a solidifying agent. In some embodiments, the MS medium is supplemented with at least one of IAA or BA, sucrose, and agar.

Depending on their chemical makeup, different types of plants will react differently to various types of plant medium. The medium selected should be compatible with the type of plant being used to fabricate the metallic nanoparticles. In some embodiments, a *Medicago sativa* plant is used with an MS medium. In some embodiments, the MS medium in which the *Medicago sativa* cells are suspended is supplemented with at least one auxin, such as for example IAA; at least one cytokinin, such as for example BA; or a combination thereof.

The metal salt provides the source of the metal that the plant will use to fabricate the metallic nanoparticles. Any suitable metal salt solution can be used. In some embodiments, the metal salt is the salt of at least one of copper, titanium, aluminum, gold, silver, zinc, iron, cerium, or a combination thereof. In some embodiments, the metal salt is a gold salt. In some embodiments, the salt is a chloride, acetate, carbonate, citrate, cyanide, fluoride, nitrate, oxide, phosphate, sulfate, or a combination thereof. In some embodiments, the metal salt is potassium gold chloride ($KAuCl_4$).

As noted hereinabove, the plant cells suspended in the plant medium intake the metal salt, and manufacture the metallic nanoparticles within the cells. Advantageously, these metallic nanoparticles can be isolated from plant borne contaminants, medium components, and unreacted metal salts, and purified. If desired, the isolated metallic nanoparticles can be dried. Any suitable method can be used to extract the metallic nanoparticles. In some embodiments, the metallic nanoparticles are extracted by at least one of sonication, centrifugation, washing, gel-filtration or molecular sieve chromatography. In some embodiments, the metallic nanoparticles are extracted by sonication, centrifugation and passing the metal-nanoparticle-containing lysate through a gel-filtration column. One or more washes with water, for example nanopure water, can also be used. Any suitable gel filtration column may be used to perform the gel filtration, such as for example, a Sephadex G25, G50 or G100 column.

Isolated nanoparticles can be characterized for their shape, size and functions. The plant cell suspension method produces metallic nanoparticles having a variety of shapes and sizes. In some embodiments, the method produces metallic nanoparticles having a morphology of at least one of spheres, triangles, pentagons, pentagonal pyramids, hexagons, rods, rhomboids, nanoplates, or combinations thereof. In some embodiments, substantially all, or all of the metallic nanoparticles, have the same morphology. In some embodiments, the metallic nanoparticles have more than one type of morphology. In some embodiments, the metallic nanoparticles have a size of from about 5 nm to about 250 nm. In some embodiments, the metallic nanoparticle size is between about 15 nm and about 75 nm. In some embodiments, the metallic nanoparticle size is between about 30 nm and about 50 nm.

It was unexpectedly discovered that the shape and size of the metallic nanoparticles can be tuned by controlling the concentration of the metal salt solution in the plant cell suspension. For example, in some embodiments, at least 90% of nanoparticles induced under the treatment of from about 5 to about 15 ppm of a metal salt are spherical, and other particle shapes (for example, triangles, pentagons and hexagons) increase in proportion to an increase in metal salt concentration. In some embodiments, a small proportion of spherical particles (15-20 nm) are common to all treatments, regardless of the metal salt concentration. In some embodiments, the concentration of the metal salt solution in the plant cell suspension ranges from less than 10 ppm to about 250 ppm. In some embodiments, the concentration of the metal salt solution in the plant cell suspension ranges from less than 25 ppm to about 150 ppm. In some embodiments, the concentration of the metal salt solution in the plant cell suspension ranges from about 125 ppm to about 150 ppm. The ability to tune the metallic nanoparticles is desirable, because the size and shape of the metallic nanoparticles impacts their properties, such as for example their optical and electrical properties, and thus their uses. For example, triangular nanoparticles are useful for catalysis, medicine, and cancer-therapy, due to their unique shape, and large surface areas; and spherical nanoparticles are useful for biomedical applications, including drug delivery, gene therapy, cancer therapy and antibody diagnostics, due to their unique shape, surface chemistry, and mono-disperse and optical properties.

It was unexpectedly discovered that the metallic nanoparticles made using the plant cell suspension have a surface chemistry that is different from nanoparticles made by other methods. Additionally, the nanoparticle surface chemistry can differ depending upon the type of plant cells, and the controlled conditions of culture that are used to make the metallic nanoparticles. For example, metallic nanoparticles that are fabricated in *Medicago sativa* cells have moieties attached to the nanoparticle surface, and these moieties include at least one of aliphatic alcohol, alkyl, hydroxyl, or amino functional groups. In some those embodiments where a different type of plant is used to make the metallic nanoparticles, the surface chemistry can be different. The unique surface chemistry of the metallic nanoparticles made in plant cell culture elicit cytotoxicity and immune reactivity similar as those produced by chemically synthesized counterparts, and they are therefore effective for the same type of uses as those made by conventional method.

In some embodiments, the metallic nanoparticles are used in the manufacture of medicaments. Such medicaments can be used as antibacterial compositions for killing or preventing the growth of microbes in any area of a subject's body, such for example an oral cavity, nose, rectum, vagina or other localized lesions. In some embodiments, the metallic nanoparticles are used as a photosensitizer, or as conjugates for use in radiotherapy, brachytherapy or photosensitization of a tissue of interest. In some embodiments, the cell culture-derived nanomaterials are used as a catalyst or biocatalyst in water filtration systems or air pollution treatment operations.

In some embodiments, the nanoparticles can be combined with a second active agent, such as a chemotherapy or biological composition, to increase the therapeutic effects of the second active agent.

As used herein, and in the appended claims, the singular forms "a", "and" and "the" include plural references, unless the context clearly dictates otherwise.

The term "about" refers to a range of values which would not be considered by a person of ordinary skill in the art as substantially different from the baseline values. For example, the term "about" can refer to a value that is within 20%, 15%, 10%, 9%, 8%, 7%, 6%, 5%, 4%, 3%, 2%, 1%, 0.5%, 0.1%, 0.05%, or 0.01% of the stated value, as well as values intervening such stated values. Context will dictate which value, or range of values, the term "about" can refer to in any given instance, throughout this disclosure.

Where a value of ranges is provided, it is understood that each intervening value, between the upper and lower limit of that range, and any other stated or intervening value in that stated range, is encompassed within the invention. The upper and lower limits of these smaller ranges, which can independently be included in the smaller ranges, is also encompassed within the invention, subject to any specifically excluded limit in the stated range.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention.

The following non-limiting examples serve to further illustrate the present invention.

EXAMPLES

The following examples describe the synthesis and characterization of the metallic nanoparticles.

Example 1. Synthesis and Recovery of Gold Nanoparticles

Continuously Growing Plant Cell Culture:

Hypocotyl regions dissected out from one-week-old seedlings of *M. sativa* (germinated on water agar medium) was inoculated on MS medium38, pH 5.7, supplemented with 30% sucrose, 0.8% agar, 0.2 mg/L IAA and 0.2 mg/L BA. After two weeks, the callus mass derived from the explant was transferred to liquid medium with the same composition. Conical flasks containing $\frac{1}{5}^{th}$ volume of the culture was grown on an orbital shaker with 100 rpm at 27° C. Callus clumps remaining in the medium were removed after two days. After one week, cell suspension was collected, discarding the clumps of callus remaining in the bottom. The process of clump removal from the growing suspension was repeated three times to achieve a homogenous stock of cell suspension. The single cell nature of the culture was confirmed by microscopic examination. Sub culturing was done once in every two weeks, by spinning down cells at 2000 rpm for 10 min, and adding fresh medium following the removal of the old one.

Testing $KAuCl_4$ Tolerance of *Medicago Sativa* Cells in Culture:

To determine the $IC_{50}$ of $KAuCl_4$, the filter sterilized stock solution of $KAuCl_4$ (prepared in deionized water) was added at different concentrations (10-200 ppm) to 20 mL culture having a cell density of 20,000 cells/mL and incubated on the shaker for 2 weeks. Culture aliquots (1 mL) were collected at an interval of 48 h, spun at 2000 rpm for 10 min, stained with phosphate buffered Trypan Blue, and dead cells were counted using a haemocytometer. Percentage of cell death was determined from the total cell number.

Results: As heavy metals are generally toxic to living cells, tolerance of *M. sativa* cells in suspension to $KAuCl_4$ was determined by exposing the culture to its various concentrations (10-200 ppm). The highest concentration (200 ppm) affected cell viability by eliminating 25% cells from the culture after two weeks of continuous growth in the liquid medium.

Synthesis of Gold Nanoparticles and Characteristics of the Cell Mediated Nanoparticle Synthesis:

$KAuCl_4$ was supplemented to the cell culture at the rate of 10-200 ppm and incubated on a shaker for 24 h, in darkness. Aliquots (1 mL) of the culture were collected in Eppendorf tubes, and centrifuged for 2 min (14,000 rpm), and the medium was removed. Same amount of nanopure water was added to wash away traces of medium and the unreacted gold. After 5 repeated washes, the cells were allowed to re-suspend in 100 μL of water, and lysed using a sonicator for 2 min, constituting an amplification cycle of 80% intensity with a pulse for 20 sec and off time for 10 sec.

Results: When the growing cell culture was supplemented with various concentrations of $KAuCl_4$, the characteristic color change took place in the reaction mixture from golden yellow to purple/violet after 18-20 h. The reduction reaction was confined within the *Medicago* cells, since the residual liquid medium remained colourless after pelleting down the cells. MS medium when separately incubated with $KAuCl_4$, in the absence of live cells, no reactions proceeded to form nanoparticles. The nanoparticles formed were identified as AuNPs by SEM-EDX of the cell lysate and their intracellular fabrication was ascertained by TEM analysis of ultrathin sections. This, in turn, ruled out the possibilities for involvement of any of the components of the nutrient medium.

Effect of $KAuCl_4$ Concentration on Particle Size: Analysis of nanoparticle morphologies revealed a significant positive correlation between the feeding concentration of KAuCl4 and the size of the AuNPs formed. Statistical analysis (ANOVA) clearly indicates the significant variations ($p<0.01$) among different groups. Spheres, triangles, pentagons and hexagons were the major types of particles found distributed throughout the samples analyzed (see FIG. 1A-1D). A small proportion of rods and rhomboids were also found. Approximately, 95% of nanoparticles induced under the treatment of 10 ppm $KAuCl_4$ were spherical whereas other particle shapes (triangles, pentagons and hexagons) increased in proportion to an increase in $KAuCl_4$ concentration. A small proportion of spherical particles (15-20 nm) were common to all treatments. A linear progression in particle size was evident in accordance with the increase in $KAuCl_4$ concentration (see FIG. 1A-1E). Diameter of particles formed under different concentrations of $KAuCl_4$ ranged between 15-75 nm. In addition to the solid particles, translucent triangular and hexagonal nanoplates were were also observed in samples treated with higher concentrations of $KAuCl_4$ (see FIGS. 1C and 1D,). Even though the effect of pH was studied by altering pH of the nutrient medium (at $KAuCl_4$ 100 ppm), its effect was not found significant (see FIGS. 1F-1H).

Recovery of Gold Nanoparticles From Plant Cells:

Cells harboring the nanoparticles were collected by centrifugation, and lysed by sonication as described above. Cell debris was separated by centrifugation at 200 g (1400 rpm) for 2 min. Supernatant (1 mL) was then loaded on to Sephadex G100 (medium) column with a bed volume of 12 cm×1.8 cm (height×diameter) equilibrated with water. Fractions of 1 mL were eluted with water from the column, at a flow rate of 1 mL/min. Collected fractions were scanned on UV-Vis spectrophotometer (Perkin Elmer, Lambda XLS+) at 200-900 nm. SDS (sodium dodecyl sulfate solution) was added to a final concentration of 0.1%, vortexed briefly, and centrifuged at 6,000 g (7,900 rpm) for 30 min at 4° C., and the supernatant removed, followed by the addition of fresh nanopure water. Efficiency of gel filtration and the washing step in removing plant cell borne contaminants was verified by testing the total protein content by Bradford test and the presence of nucleic acids by running on 1% agarose gel. Individual fractions were scanned on FT-IR (Fourier-transform infrared) spectrometer (Perkin Elmer, Spectrum 100) at 600-4000 nm, to detect the presence of particles.

Results: As noted above, AuNPs synthesized by the cells were separated from plant borne contaminants, medium components and unreacted $KAuCl_4$ by passing through Sephadex G100 column. Particles migrated through the column together as a purple band, facilitating the monitoring of sample migration and fraction collection. Eluted fractions produced absorbance peak around 540 nm, which is characteristic to AuNPs, due to the surface plasmon band. Height of the peaks varied according to color intensity of the fractions (see FIG. 2A). Minimal shift in absorption maxima was observed among various fractions eluted, which was supposed to be due to similarity in size of the particles (see FIG. 2B). Almost all fractions showed a characteristic absorption peak at NIR (near-infrared region) region, indicating the abundance of triangular or polyhedral particles rather than spherical. This was later confirmed by fractionwise analysis in TEM (transmission electron microscopy).

Figures 2A, 2B, 2C, 2D, 2E:
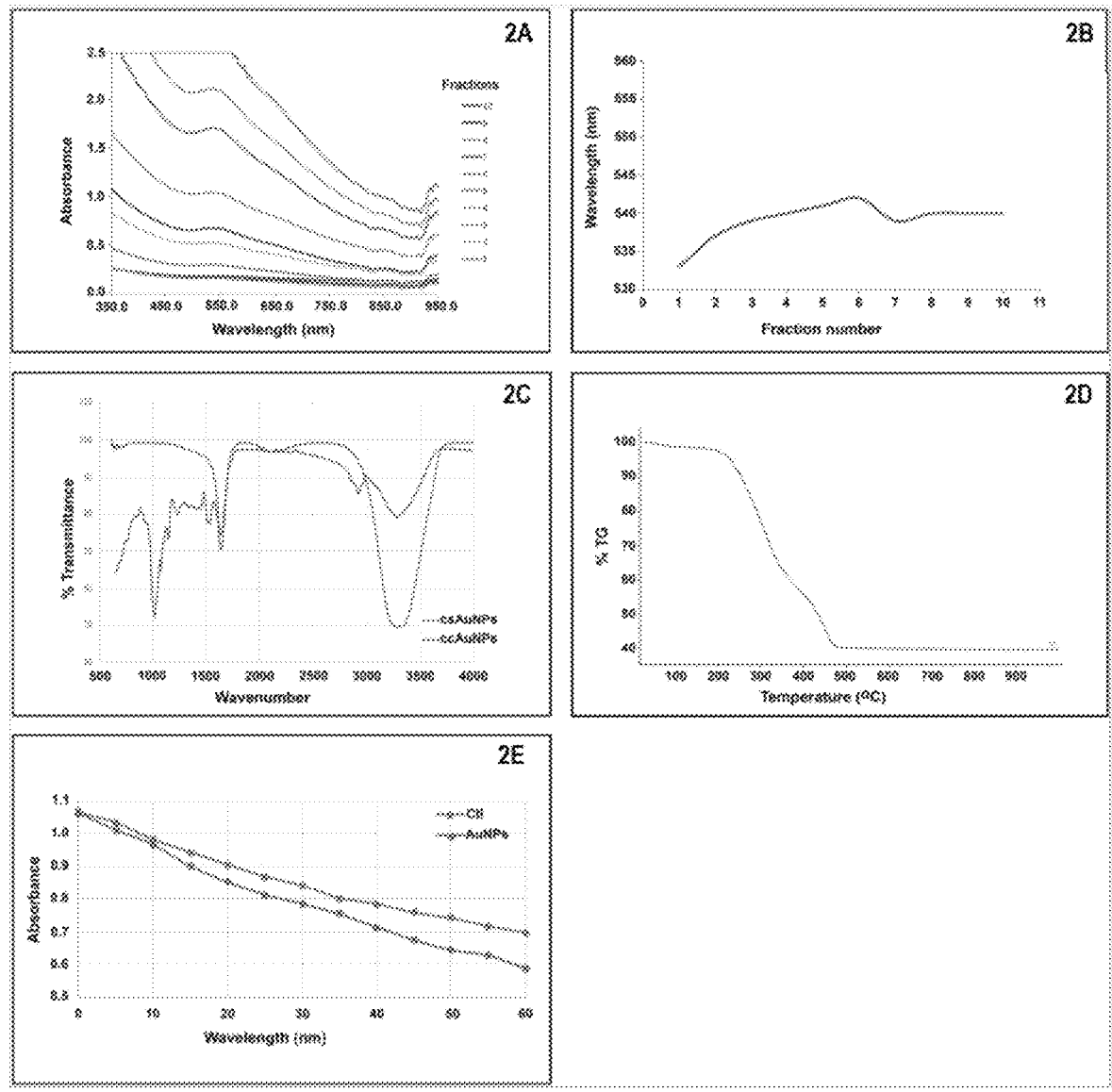
FIGS. 2A-2E represent charts demonstrating the purification and characterization of AuNPs from the cells of *Medicago sativa*.

FT-IR scans of these fractions showed the presence of aliphatic alcohol, alkyl, hydroxyl/amino groups on the surface (see FIG. 2C). Thermo Gravimetric Analysis of air dried nanoparticles demonstrated significant weight loss between 225° C. and 475° C., indicating the disintegration of these functional groups at this temperature range (see FIG. 2D).

Figures 3A, 3O:
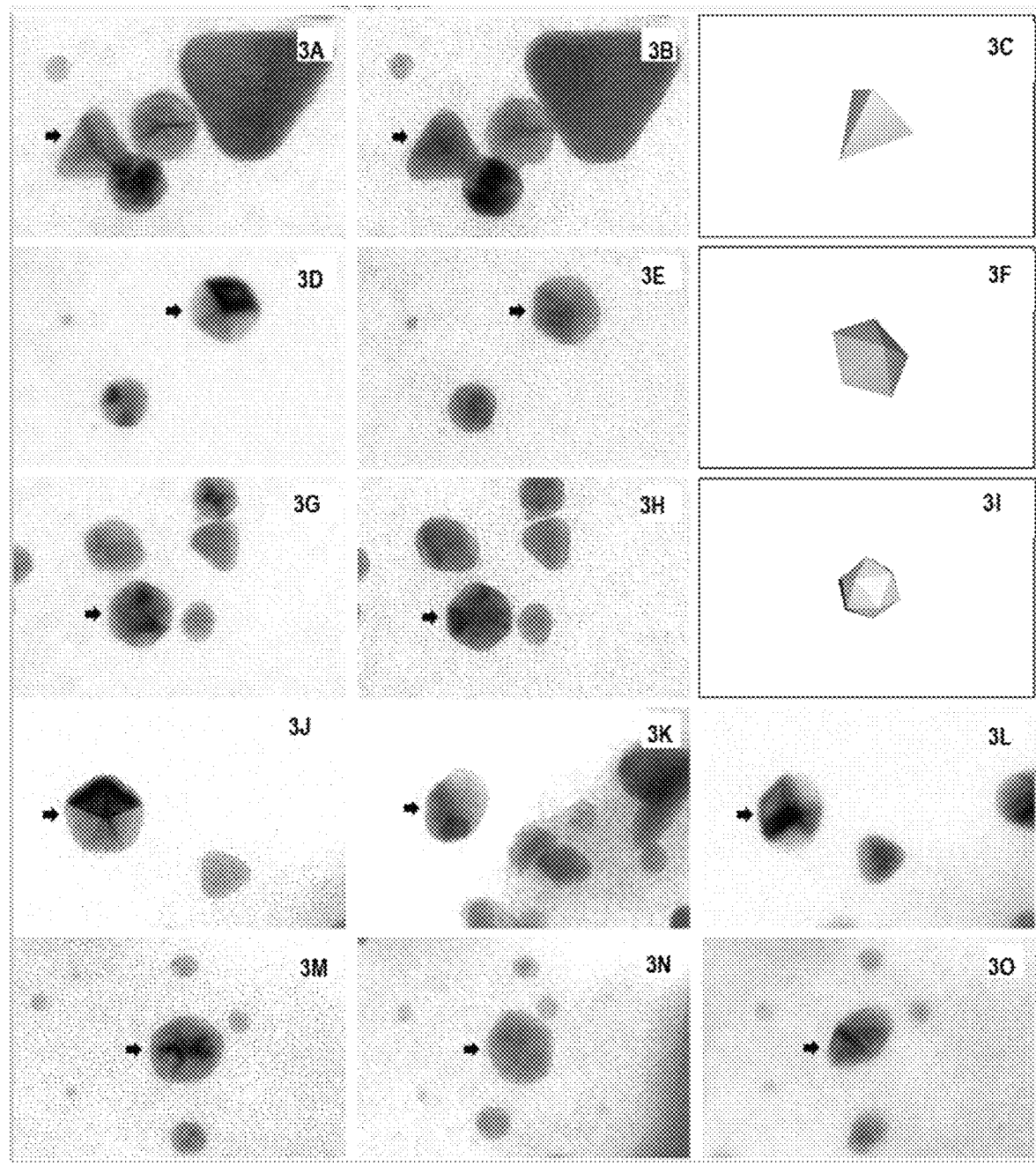
FIGS. 3A-3O represent images of isolated AuNPs.

Morphological Characterization of AuNPs Using Stereo TEM: Stereo images captured in a regular TEM displayed differential shading patterns according to the angle of rotation, which was due to the differential scattering of the electron beam on their faces. This analysis helped to distinguish between triangular plates and tetrahedrons which appeared merely as triangles in regular TE (transmission electron) micrographs (see FIG. 3A-3C). Pentagons were discovered to be pentagonal prisms (see FIG. 3D-F) whereas those appeared as hexagons were identified as icosahedrons under our image capture technique based on stereomicroscopy (see FIG. 3A-I). Pictures taken at three consecutive angles of 45° intervals proved that the particles appearing as rhomboids in regular TEM images were not true rhomboids, but pentagonal pyramids having two five sided opposite faces (see FIG. 3J-O).

Example 2. Catalytic Activity Testing

Assay for Catalytic Activity:

Catalytic activity of the isolated particles was tested in the reduction reaction of methylene blue by $SnCl_2$, in presence of SDS. 100 μL of nanoparticle suspension in water (OD 1 at 550 nm) was added to 3 ml SDS (0.01 M), 10 μL methylene blue (0.5 mM) and 50 μL $SnCl_2$ (0.05 M). Absorbance at 500-800 nm at 5 min intervals was recorded to monitor the reaction rate. A control reaction was run in parallel adding 100 μL water instead of the nanoparticle suspension.

Results: Isolated nanoparticles demonstrated catalytic activity in the reduction reaction of methylene blue by stannous chloride. Progression of the reaction was monitored by observing the height of absorbance peak at 660 nm. Readings taken for 1 h at 5 min intervals indicated successive reduction in absorbance in test as well as control groups (see FIG. 2E). Addition of nanoparticle suspension to the reaction mixture causing about 32% increase in the reaction rate was a clear proof of the catalytic activity (see FIG. 2E).

Example 3. Characterization of Gold Nanoparticles

Electron Microscopy

Sonicated samples (5 μL) were loaded on 100 mesh formvar coated copper grid. Particles were allowed to settle for 5 min, and the excess cell lysate was blotted and dried on a hot plate at 50° C. for 10 min. Samples were viewed at 100 kV and images captured at 66,000 X by 120 CX TEM (JEOL JEM). Scanned images (1200 dpi) of the particles were subjected to morphological analysis using the software Iridium Ultra version 1.4 (www.ixrfsystems.com). For unravelling the three dimensional features of the particles, pictures were taken at 100,000×, rotating the grid at different angles. Energy Dispersive X-ray Spectroscopy (EDS) of the cell lysate was done by loading the sample on carbon ribbon and viewed at an accelerating potential of 20 kV under high vacuum mode with backscatter detector in JSM-5400LV scanning electron microscope (JEOL) equipped with IXRF EDS system with Moxtek AP3.3 light element entrance window.

Results: The AuNPs synthesized were found accumulated inside the cells on the analysis of thin sections by TEM, validating the intracellular fabrication mediated by the internal milieu of the cell. This, in turn, rules out the possibilities for involvement of any of the components of the nutrient medium.

Example 4. In Vitro Cytotoxicity Testing of Gold Nanoparticles

Toxicity testing is a prerequisite for determining the suitability of the AuNPs for various diagnostic and therapeutic applications. Toxicity of the isolated nanoparticles on human epithelial type 2 cell (HEp-2: ATCC CCL-23) and mouse mammary gland tumor cell line (4T-1: ATCC CRL-2539) was tested by MTT (3-(4,5-dimethylthiazol-2-yl)-2,5-diphenyltetrazolium bromide, a tetrazole) assay. HEp-2 cells were maintained in Minimum Eagle's Medium (MEM) supplemented with 10% fetal bovine serum (FBS), L-glutamine (2 mM), PKS [penicillin (75 U/mL), kanamycin (100 μg/mL) and streptomycin (75 μg/mL)]. 4T-1 cells were maintained in Dulbecco's MEM Glutamax, supplemented with 10% FBS, and 1% Antibiotic-Antimycotic (100×). Cells were grown to achieve a density of 17,000 cells per well, in 96 well tissue culture plates. Following overnight incubation, the culture medium was replaced by fresh medium with serial dilutions of nanoparticle, starting from 0.7 to 25m/mL. Percentages of cell viability after 24 and 48 h incubation were determined by the assay.

Figures 4A, 4B, 4C, 4D, 4E:
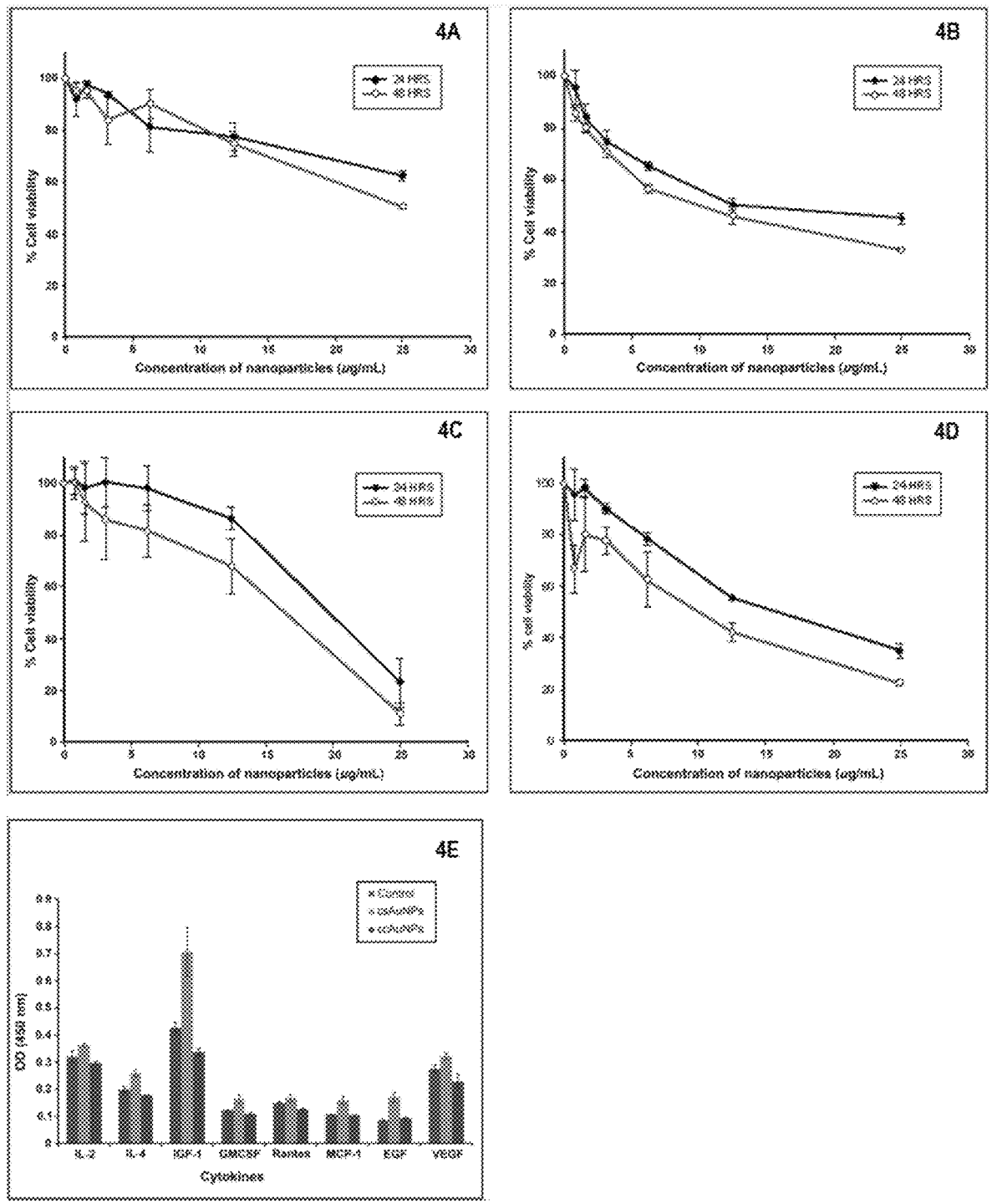
FIGS. 4A-4E represent charts demonstrating AuNPs synthesized by cell culture (ccAuNPs) have cytotoxicity and immune reactivity comparable to those synthesized by chemical synthesis citrate reduction (csAuNPs)

Results: As noted hereinabove, toxicity of the isolated nanoparticles were tested by MTT assay. The cell culture-synthesized nanoparticles (ccAuNPs) inhibited approximately 50% human epithelial cells (HEp-2) while chemically synthesized nanoparticles (csAuNPs) induced inhibition in 60% of cells in the same cell line (see FIGS. 4A and 4B). Interestingly, effects on cancer cell line 4T-1 were significantly different for both types of nanomaterials: ccAuNPs caused 70-90% cell death while csAuNPs had mortality rate of 50-70% for 4T1 cancer cell line at the inhibitory concentration, 25 μg/ml, after 24 and 48 h of incubation (see FIGS. 4C and 4D).

Example 5. In Vitro Cytotoxicity Testing of Gold Nanoparticles

Cytokine Detection by ELISA

Lab mice C/57-BL6/J (10-week-old, female mice, 5 per group) were intra-peritoneally injected with 200 μL (333m/kg body weight) of cell culture-synthesized nanoparticles (ccAuNPs) or chemically synthesized particles (csAuNPs). Control was maintained with 200 of PBS (phosphate buffered saline). Blood was harvested after 15 days of exposure in mice. Blood was stored overnight before processing for the serum. Serum samples were further processed using Custom Mouse ELISA Strip (Signosis, Santa Clara, CA), and absorbance was measured by Synergy plate reader at 450 nm. The testing protocol "Assessment of Plant-derived, Ecofriendly Gold Nanoparticles using an Animal System" was approved by Western Kentucky University's Institutional Animal Care and Use Committee (Animal Welfare Assurance #A3558-01) and was assigned the following designation (16-09). The approved protocol remains valid from Dec. 8, 2016 to Dec. 7, 2019.

Results: The ccAuNPs were tested for their inflammatory responses in vivo. The levels of cytokines and growth factors, including IL-2, IL-4, IGF-1, GMCSF, Rantes, MCP-1, EGF and VEGF (see FIG. 4E) in mice were not significantly different (p>0.05) between two groups of mice challenged with 200 μL of ccAuNPs or csAuNPs, and were comparable to the unchallenged control. Expression pattern of few genes associated with inflammatory responses further testifies the efficacy of ccAuNPs.

Statistical Analysis

Statistical analyses were carried out in Microsoft Excel 2010. Significance of the results of particle size and shape analyses was verified by ANOVA. Results of the tolerance test of plant cells to KAuCl4, toxicity testing of AuNPs in animal cell lines, cytokine detection and real-time PCR in mice were analysed for significance using t-test. Level of significance was kept at 0.05 for all the analyses.

Analysis of nanoparticle morphologies revealed a significant positive correlation between the feeding concentration of KAuCl4 and the size of the AuNPs formed. Statistical analysis (ANOVA) clearly indicates the significant variations (p<0.01) among different groups.

What is claimed is:

1. A method of synthesizing metallic nanoparticles comprising the steps of:
   (i) providing at least a portion of at least one plant, wherein the plant is *Medicago sativa*,
   (ii) placing the at least one portion of the plant in a plant cell suspension medium and culturing the at least one portion of the plant until a plant cell suspension comprising single plant cells is formed,
   (iii) adding at least one metal salt solution comprising potassium gold chloride (KAuCl$_4$) to the plant cell suspension and continuing to culture the plant cell suspension until, metallic nanoparticles form within the plant cells, and
   (iv) isolating the metallic nanoparticles from the cells.

2. The method according to claim 1, wherein the plant cell suspension medium comprises or has added to it, at least one of, a macronutrient, micronutrient, vitamin, amino acid, nitrogen supplement, carbon source, energy source, organic supplement, growth regulator, or solidifying agent.

3. The method according to claim 1, further comprising the step of adding at least one growth regulator to the plant cell suspension medium.

4. The method according to claim 3, wherein the growth regulator is selected from the group consisting of an auxin, cytokinin, gibberellin, abscisic acid, and a combination thereof.

5. The method according to claim 3, wherein the growth regulator is selected from the group consisting of indole-3-acetic acid (IAA), 6-benzyloaminopurine (BAP or BA), and a combination thereof.

6. The method according to claim 1, further comprising the step of adding at least one growth regulator, carbohydrate and solidifying agent to the plant cell suspension medium.

7. The method according to claim 1, further comprising the step of drying the metallic nanoparticles.

8. The method according to claim 1, wherein the portion of the plant is selected from the group consisting of at least a portion of a leaf, stem, root, flower, fruit, seed, and a combination thereof.

9. The method according to claim 1, wherein the metallic nanoparticles have a morphology selected from the group consisting of spheres, triangles, pentagons, pentagonal pyramids, hexagons, rods, rhomboids, nanoplates, and a combination thereof.

10. The method according to claim 1, wherein the metallic nanoparticles have a length ranging from about 5 nm to about 250 nm.

11. The method according to claim 1, wherein the metallic nanoparticles have a length ranging from about 15 nm to about 75 nm.

12. The method according to claim 1, wherein at least one of the morphology or size of the metallic nanoparticle can be controlled by adjusting the concentration of the metal salt solution in the plant cell suspension.

13. The method according to claim 1, wherein the concentration of the metal salt solution in the plant cell suspension ranges from less than 10 ppm to about 250 ppm.

14. The method according to claim 1, wherein the concentration of the metal salt solution in the plant cell suspension ranges from less than 25 ppm to about 150 ppm.

15. The method according to claim 1, wherein the concentration of the metal salt solution in the plant cell suspension ranges from about 125 ppm to about 150 ppm.

16. The method according to claim 1, wherein the metallic nanoparticles are isolated from the plant cells using a process selected from the group consisting of sonication, centrifugation, washing, gel column filtration, molecular sieve chromatography, and a combination thereof.

17. The method according to claim 1, wherein each metallic nanoparticle has attached thereto at least one moiety.

18. The method according to claim 17, wherein the moiety is selected from the group consisting of an aliphatic alcohol, alkyl, hydroxyl, amino, functional group, and a combination thereof.

* * * * *